United States Patent [19]

Takaya et al.

[11] Patent Number: 5,497,779
[45] Date of Patent: Mar. 12, 1996

[54] PULSE WAVE DETECTING APPARATUS

[75] Inventors: Masami Takaya, Aichi; Hideo Nishibayashi, Inuyama, both of Japan

[73] Assignee: Colin Corporation, Aichi, Japan

[21] Appl. No.: 207,179

[22] Filed: Mar. 8, 1994

[51] Int. Cl.⁶ ..................................................... A61B 5/00
[52] U.S. Cl. ........................... 128/672; 128/687; 128/690
[58] Field of Search ................................... 128/672, 677, 128/687–690

[56] References Cited

U.S. PATENT DOCUMENTS

| | | |
|---|---|---|
| 4,901,733 | 2/1990 | Kaida et al. . |
| 4,951,679 | 8/1990 | Harada .................................... 128/687 |
| 5,099,853 | 3/1992 | Uemura et al. . |
| 5,139,026 | 8/1992 | Niwa ....................................... 128/687 |

FOREIGN PATENT DOCUMENTS

| | | |
|---|---|---|
| 0401382 | 12/1990 | European Pat. Off. . |
| 0452578A1 | 10/1991 | European Pat. Off. . |
| 1-285244 | 11/1989 | Japan . |
| 2257529 | 1/1993 | United Kingdom . |
| WO93/15653 | 8/1993 | WIPO . |

*Primary Examiner*—Angela D. Sykes
*Assistant Examiner*—Robert L. Nasser, Jr.
*Attorney, Agent, or Firm*—Oliff & Berridge

[57] ABSTRACT

A pulse wave detecting apparatus including a pulse wave sensor having a press surface and including at least one array of pressure sensing elements provided in the press surface; a pressing device which produces a pressing force to press the press surface of the pulse wave sensor against an arterial vessel via body surface; a regulating device for changing the pressing force of the pressing device applied to the pulse wave sensor, determining an optimum value of the pressing force based on at least one of the pulse wave signals generated from the pressure sensing elements, and holding the pressing force of the pressing device at the thus determined optimum value; a lower-peak variation determining device for determining a lower peak of at least one pulse of each of the pulse waves represented by the respective pulse wave signals from the pressure sensing elements, the lower-peak variation determining device iteratively determining a variation of the respective lower peaks of the pulse waves with respect to the array of pressure sensing elements after the pressing force of the pressing device is held at the optimum value; and a judging device for judging whether a pressing condition of the pulse wave sensor on the body surface is stable, based on change of the lower-peak variations determined by the lower-peak variation determining device.

11 Claims, 11 Drawing Sheets

 FIG.8(ℓ)

4,497,779

PULSE WAVE DETECTING APPARATUS

BACKGROUND OF THE INVENTION

1. Field of the Invention

The present invention relates to a pulse wave detecting apparatus which presses a pulse wave sensor against an arterial vessel of a living body or subject via body surface above the artery and detects a pressure pulse wave produced from the artery.

2. Related Art Statement

There is known a pulse wave detecting device including (a) a pulse wave sensor having a press surface and including a plurality of pressure sensing (PS) elements provided in one or more arrays in the press surface, the pulse wave sensor being adapted to be pressed against an arterial vessel of a living subject via a body surface of the subject such that a direction of the array or arrays of PS elements intersects a direction of extension of the artery, so that each of the pressure sensing elements detects a pressure pulse wave produced from the artery and generates a pulse wave signal representing the detected pulse wave, (b) a pressing device which produces a pressing force to press the press surface of the pulse wave sensor against the artery via the body surface, and (c) regulating means for continuously changing the pressing force of the pressing device applied to the pulse wave sensor, determining an optimum value of the pressing force based on one or more of the pulse wave signals generated from the PS elements, and holding the pressing force of the pressing device at the thus determined optimum value. The prior apparatus reads in the pulse wave signal or signals supplied from one or more of the PS elements pressed with the optimum pressing force, and obtains the pressure pulse wave of the subject based on the pulse wave signal or signals. The prior apparatus is disclosed in, for example, Japanese Patent Application laid open for inspection purpose under Publication No. 1(1989)-285244.

However, in the prior pulse wave detecting device, the condition of pressing of the pulse wave sensor against the body surface (e.g., manner of contact of the former with the latter) may change due to, for example, motion of the subject (e.g., motion of his or her wrist on which the sensor is being worn). In this event, the reading or detected magnitude of the pulse wave is adversely affected. The detected pulse wave may contain both change due to natural change of blood pressure of the subject and change due to artificial change of the pressing condition of pulse wave sensor. Thus, the accuracy of detection of the prior device is not satisfactory.

SUMMARY OF THE INVENTION

It is therefore an object of the present invention to provide a pulse wave detecting apparatus which continuously detects a pressure pulse wave of a living subject with high accuracy.

The Applicants have intensively studied for achieving the above object, and have found that the variation (i.e., distribution or pattern) of the respective lower peaks of the pulse waves detected through the pressure sensing elements with respect to the array of pressure sensing elements, with the pulse wave sensor being pressed with the optimum pressing force, is intimately related to the condition of pressing of the pulse wave sensor against the body surface of the subject. The present invention has been developed based on this discovery.

The above object has been achieved by the present invention, which provides a pulse wave detecting apparatus for detecting a pulse wave from a living subject, the pulse wave comprising a plurality of pulses produced from an arterial vessel of the subject in synchronism with heartbeat of the subject, comprising (a) a pulse wave sensor having a press surface and including at least one array of pressure sensing elements provided in the press surface, the press surface of the pulse wave sensor being adapted to be pressed against the arterial vessel of the living subject via a body surface of the subject such that a direction of the array of pressure sensing elements intersects a direction of extension of the arterial vessel, so that each of the pressure sensing elements detects the pulse wave produced from the arterial vessel and generates a pulse wave signal representing the detected pulse wave, (b) a pressing device which produces a pressing force to press the press surface of the pulse wave sensor against the arterial vessel via the body surface, (c) regulating means for changing the pressing force of the pressing device applied to the pulse wave sensor, determining an optimum value of the pressing force based on at least one of the pulse wave signals generated from the pressure sensing elements, and holding the pressing force of the pressing device at the thus determined optimum value, (d) lower-peak variation determining means for determining a lower peak of at least one pulse of each of the pulse waves represented by the respective pulse wave signals from the pressure sensing elements, the lower-peak variation determining means iteratively determining a variation of the respective lower peaks of the pulse waves with respect to the array of pressure sensing elements after the pressing force of the pressing device is held at the optimum value, and (e) judging means for judging whether a pressing condition of the pulse wave sensor on the body surface is stable, based on change of the lower-peak variations determined by the lower-peak variation determining means.

In the pulse wave detecting apparatus constructed as described above, the lower-peak variation determining means determines iteratively determines a variation of the respective lower peaks of the pulse waves with respect to the array of pressure sensing elements after the pressing force of the pressing device is held at the optimum value, and the judging means judges whether a pressing condition of the pulse wave sensor on the body surface is stable, based on change of the lower-peak variations determined by the lower-peak variation determining means. When the judging mans provides a negative judgment that the pressing condition of the pulse wave sensor on the body surface is not stable, i.e., has changed, the regulating means may be operated for updating the optimum pressing force of the pressing device, thereby changing the pressing condition of the pulse wave sensor. Alternatively, the present apparatus may further comprise an informing device which informs an operator or user of the negative judgment, so that the operator or user can recognize that the pressing condition of the pulse wave sensor has changed. Thus, the accuracy of detection of the present apparatus is improved.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings in which:

FIGS. 8(a) to 8(l) are views of various patterns of change of a subsequent curve MTC from a reference curve $MTC_s$, each pattern belonging to a second group of patterns, II, which indicate that the pressing condition of the pulse wave sensor is not stable.

DETAILED DESCRIPTION OF THE PREFERRED EMBODIMENTS

Figure 1:
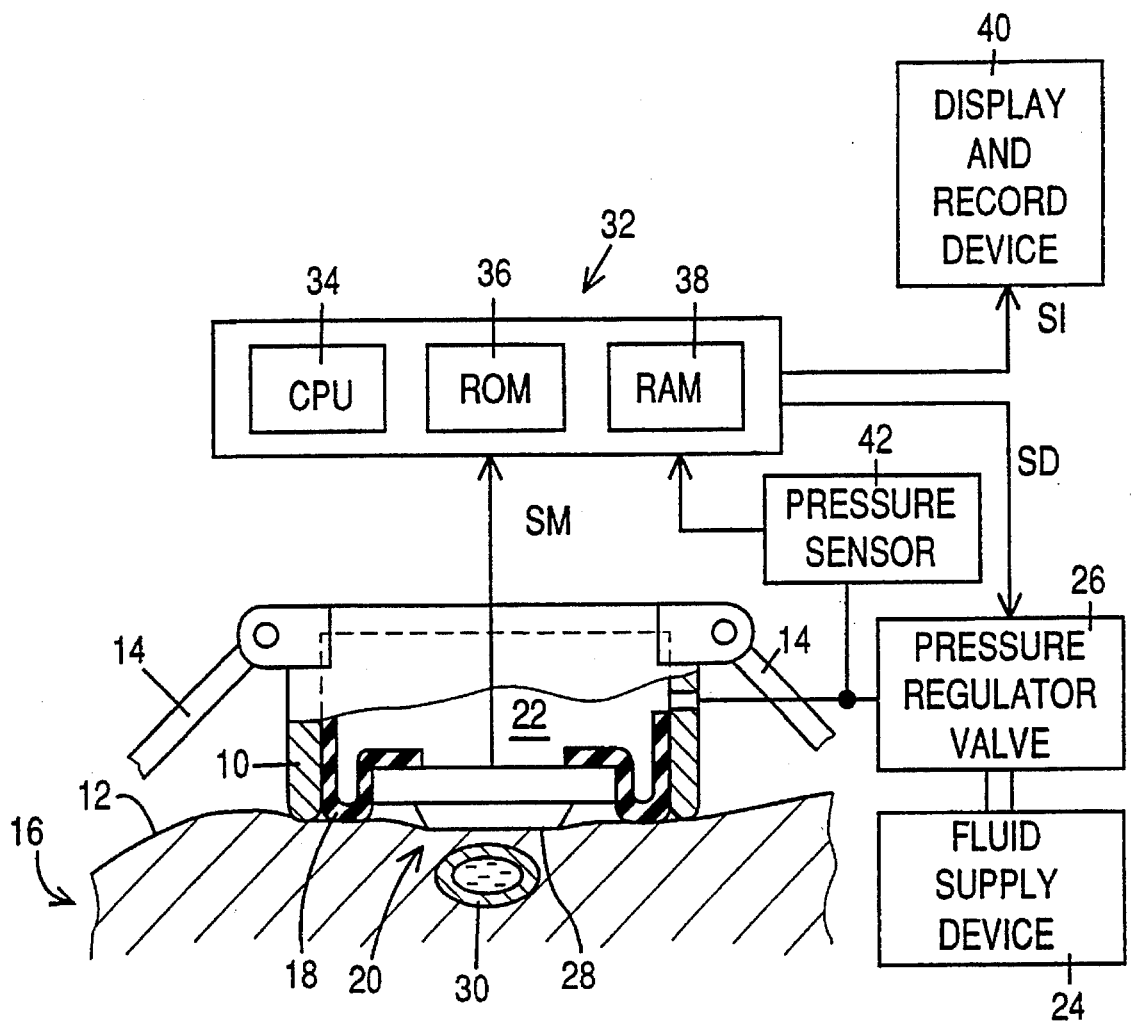
FIG. 1 is a diagrammatic view of a pulse wave detecting apparatus embodying the present invention.

Referring first to FIG. 1, there is shown a pulse wave detecting apparatus embodying the present invention. In the figure, reference numeral 10 designates a container-like housing. The housing 10 has a wall-free end closed by a pulse wave (PW) sensor 20 and a diaphragm 18. The present apparatus is detachably set on a wrist 16 of a living subject with the help of setting bands 14, 14, such that the wall-free end of the housing 10 is held in contact with body surface 12 of the subject 16. The diaphragm 18 is flexible enough to permit the PW sensor 20 to displace relative to the housing 10 and advance out of the wall-free end of the housing 10. The housing 10, diaphragm 18, and PW sensor 20 cooperate with each other to define a pressure chamber 22, which is supplied with pressurized fluid such as pressurized air from a fluid supply device 24 via a pressure regulator valve 26. A pressure sensor 42 detects the fluid pressure in the pressure chamber 22 (hereinafter, referred to as the "chamber pressure P"), and generates an electric signal representing the detected chamber pressure P. The PW sensor 20 is pressed on the body surface 12 with a pressing force corresponding to the chamber pressure P. In the present embodiment, the housing 10, diaphragm 18, fluid supply 24, and pressure regulator 26 cooperate with each other to serve as a pressing device for pressing the PW sensor 20 against the body surface 12.

Figure 2:
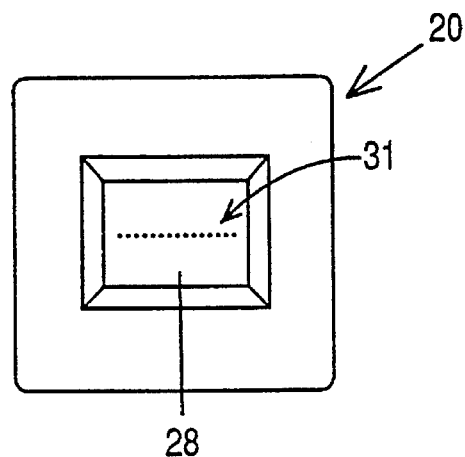
FIG. 2 is an enlarged view of a pulse wave sensor incorporated in the apparatus of FIG. 1, as seen by a person facing the press surface of the sensor in which surface an array of pressure sensing elements are provided.

As shown in FIG. 2, the PW sensor 20 has a press surface 28 defined by a semiconductor chip of, for example, monocrystalline silicon. A single array of pressure sensing (PS) elements 31 (e.g., thirty PS diodes) are provided straightly in the press surface 28. However, the PS elements 31 may be arranged in two or more arrays. The PW sensor 20 is pressed against a radial artery 30 via the body surface 12 such that the direction of the array of PS elements 31 generally perpendicularly intersects the direction of extension of the radial artery 30, so that each of the PS elements 31 detects an oscillatory pressure wave or pressure pulse wave that is produced from the radial artery 30 and is propagated to the body surface 12. A pressure pulse wave contains a plurality of pulses lack of which is produced from an arterial vessel of a living subject in synchronism with a heartbeat of the subject. The PS elements 31 are provided equidistantly from each other in the press surface 28, and the distance between the PS elements 31 is pre-selected at a sufficiently small value which enables a sufficiently great number of PS elements 31 to ride directly above the radial artery 30. Additionally, the overall length of the array of PS elements 31 is pre-selected at a greater value than the lumen or diameter of the radial artery 30. Each of the PS elements 31 generates an electric signal, i.e., pulse wave signal, SM, representing the pressure pulse wave detected thereby from the radial artery 30, and the pulse wave signals SM generated from all the PS elements 31 are supplied to a control device 32. The control device 32 also receives from the pressure sensor 42 the pressure signal representing the chamber pressure P.

Figure 5:
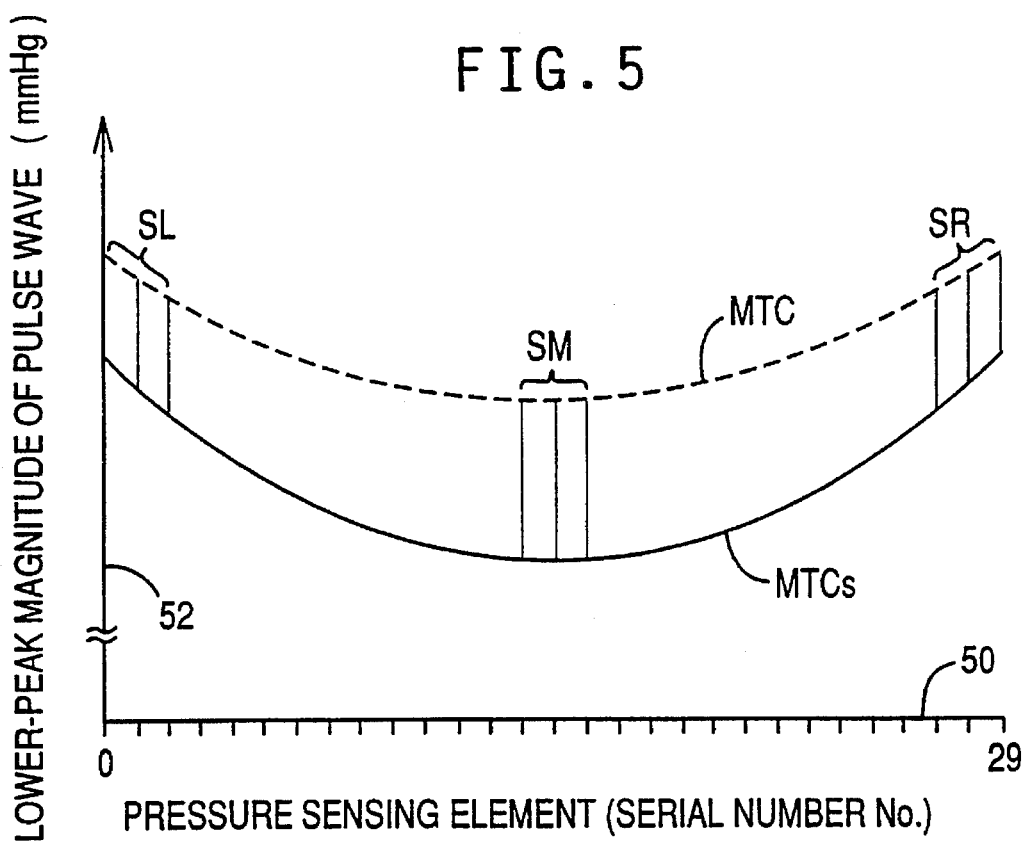
FIG. 5 is a view of a reference minimum tonogram curve, $MTC_s$, and a subsequent minimum tonogram curve, MTC, each determined at Step S9 of the flow chart of FIG. 3.

The control device 32 is essentially constituted by a microcomputer including a central processing unit (CPU) 34, a read only memory (ROM) 36, and a random access memory (RAM). The CPU 34 processes input signals according to control programs pre-stored in the ROM 36 by utilizing temporary-data-storage function of the RAM 38. Specifically, according to well-known control programs, the CPU 34 determines an optimum pressing force (in the present embodiment, optimum chamber pressure, Pa) to be applied to the PW sensor 20, and selects an optimum PS element 31a from the array of PS elements 31, based on the pulse wave signals SM supplied from the PS elements 31 while the chamber pressure P is changed. The CPU 34 supplies control signal, SD, to the pressure regulator 26 to hold the chamber pressure P at the thus determined optimum value Pa. After the chamber pressure P is held at the optimum value Pa, the CPU 34 reads in, and stores in the RAM 38, the pressure pulse wave in the form of the pulse wave signal SM supplied from the optimum PS element 31a, and supplies control signal, SI, to a display and record device 40 to display and record the thus obtained pulse wave that contains heartbeat-synchronous pulses. Meanwhile, the CPU 34 determines a lower peak of one or more pulses of the pulse wave represented by the pulse wave signal SM supplied from each of the PS elements 31. The CPU 34 determines a variation, MTC (FIG. 5), of the lower peaks of the pulse waves with respect to the array of PS elements 31, in each of periodic cycles after the chamber pressure P is held at the optimum value Pa. The CPU 34 judges whether or not the condition of pressing of the PW sensor 20 on the body surface 12 is stable, based on time-wise change of the pulse-wave lower-peak variations determined in the periodic cycles. In the event that the CPU 34 judges that the pressing condition of the PW sensor 20 is not stable, i.e., has changed due to, e.g., motion of the wrist 16, the CPU 34 updates the optimum chamber pressure Pa and holds the chamber pressure P at the updated optimum pressure Pa. Thus, the present apparatus continues to press the PW sensor 20 against the body surface 12 under the stable condition, so that the optimum PS element 31a continues to detect the pressure pulse wave (i.e., pulse wave signal SM) with high accuracy. In the following description, the pulse-wave lower-peak variation determined by the CPU 34 in each determination cycle is referred to as the "minimum tonogram curve MTC". In the present embodiment, the CPU 34 does not determine a "literal" curve MTC as illustrated in FIG. 5. However, as the number of the PS elements 31 employed increases, the pulse-wave lower-peak variation determined approaches the curve MTC.

Hereinafter there will be described the operation of the pulse wave detecting apparatus constructed as described above, by reference to the flow charts of FIGS. 3(a), 3(b), 4(a), and 4 (b).

Upon application of electric power to the present apparatus, initialization of the apparatus is carried out in a step (not shown) in which flag, F, and counters, $C_1$ and $C_2$, (described later) each are reset to zero. Subsequently, when a start and stop switch (not shown) is operated to its "ON" state, the control of the CPU 34 starts with Step S1 to operate the pressure regulator 26 so as to allow fluid to discharge from the pressure chamber 22 and subsequently supply the chamber 22 with the pressurized fluid fed from the supply device 24. Specifically, as the pressurized fluid is fed, the chamber pressure P is slowly and gradually increased up to a predetermined level, e.g., about 250 mmHg. During this chamber pressure P increasing operation, the CPU 34 receives the pulse wave signal SM from each of the PS elements 31 and the pressure signal from the pressure sensor 42 which signal represents the chamber pressure P currently being increased. The CPU 34 determines the amplitude (i.e., difference between the upper-peak and lower-peak magnitudes or between the maximum and minimum magnitudes) of each pulse of the pulse wave signal SM from each of the PS elements 31, and selects as the optimum PS element 31a one of the PS elements 31 which has supplied a maximum pulse having a maximum amplitude. Additionally, the CPU 34 determines as the optimum pressure Pa the chamber pressure P at the time of detection (or reception) of the maximum pulse from the optimum PS element 31a.

Step S1 is followed by Step S2 to hold the chamber pressure P at the optimum pressure Pa determined at Step S1. In this situation, the wall of the radial artery 30 is partially flattened under the press surface 28 of the PW sensor 20, as shown in FIG. 1. In the present embodiment, the pressure sensor 42, Steps S1 and S2 of FIG. 3(a), and a portion of the control device 32 to carry out those steps cooperate with each other to serve as regulating means for regulating the pressing force of the pressing device 18, 22, 24, 26 so as to press the PW sensor 20 with the optimum pressing force Pa.

At the following step, Step S3, the CPU 34 reads in signal SM corresponding to one pulse, from each of the PS elements 31, and stores the one-pulse signals SM from all the PS elements 31 in an appropriate area of the RAM 38. Step S3 is followed by Step S4 to operate the display/record device 40 to display and record the one-pulse signal SM supplied from the optimum PS element 31a and stored in the RAM 38. At the following step, Step S5, the CPU 34 judges whether the content of flag F is 1 (i.e., F=1). Since flag F is reset to 0 (i.e., F=0) at the time of initialization, a negative judgment is made at Step S5 in the current control cycle. Therefore, the control of the CPU 34 proceeds with Step S6.

At Step S6, the CPU 34 judges whether the CPU 34 has read in a total of eight pulses from each PS element 31 after the chamber pressure P is held at the optimum pressure Pa which has been determined for the first time after the start/stop switch is operated to the "ON" state. So long as a negative judgment is made at Step S6, Steps S3 to S6 are repeated. Meanwhile, if a positive judgment is made at Step S6, the control of the CPU 34 goes to Step S7 to determine the lower-peak (i.e., minimum) magnitude of each of the last eight pulses supplied from each PS element 31 and stored in the RAM 38. Step S7 is followed by Step S8 to determine an average of the thus determined eight lower-peak magnitudes with respect to each of the PS elements 31.

Subsequently, at Step S9, the CPU 34 determines a current minimum tonogram curve MTC as indicated in solid line in the two-dimensional coordinate system of FIG. 5. This coordinate system has an axis of abscissa 50 indicative of the serial number (No.) assigned to each PS element 31 of the PW sensor 20, and an axis of ordinate 52 indicative of the lower-peak magnitude of the pulse wave (i.e., pulse wave signal SM) in terms of mmHg. The current curve MTC is obtained by plotting in the graph a point representing the average lower-peak magnitude of each PS element 31, and connecting the plotted points with a line. Serial numbers (Nos.) are assigned to the respective PS elements 31 in the order of location thereof in the array provided in the press surface 28 of the PW sensor 20. Step S9 is followed by Step S10 to set flag F to F=1, indicating that a curve MTC has been determined at Step S9. Subsequently, at Step S11, the CPU 34 judges whether the curve MTC determined at Step S9 in the current control cycle is the first one determined after the chamber pressure P is last held at the optimum pressure Pa. Immediately after the beginning of operation of the apparatus, a positive judgment is made at Step S11, so that the control of the CPU 34 goes to Step S12. Hereinafter, the curve MTC determined immediately after the chamber pressure P is last held at the optimum pressure Pa is referred to as the "reference curve $MTC_s$".

At Step S12, the CPU 34 judges whether fifteen seconds have passed after a curve MTC (for the current control cycle, reference curve $MTC_s$) is determined at Step S9. If a negative judgment is made at Step S12, Steps S3–S5 and S12 are repeated to detect, store, display, and record respective pulses of the pulse wave from the optimum PS element 31a. Meanwhile, if a positive judgment is made at Step S12, the control of the CPU 34 goes to Step S13 to reset flag F to F=0, and subsequently the control of the CPU 34 returns to Step S5. Since flag F has just been reset to F=0 at Step S13, a negative judgment is made at Step S5. Since, at Step S6, the CPU 34 always obtains a positive result after having once obtained a positive judgment at this step, the control of the CPU 34 goes to Steps S7–S9 to determine a current minimum tonogram curve MTC as indicated in broken line in FIG. 5. Then, at Step S10, the CPU 34 sets flag F to F=1, and subsequently the control of the CPU 34 goes to Step S11. At this time, a negative judgment is made at Step S11, therefore the control of the CPU 34 goes to Step S14 and the following steps. Thus, after the determination of the reference curve MTCs, a current curve MTC is determined at regular intervals of 15 seconds.

At Step S14, the CPU 34 calculates a first-end area, SL, an optimum-portion area, SM, and a second-end area, SR, (FIG. 5) for the purpose of determining a pattern of change of the current curve MTC from the reference curve $MTC_s$. In the present embodiment, the first end area SL is calculated or approximated by summing the values obtained by subtracting the respective values on the reference curve $MTC_s$ from the corresponding values on the current curve MTC, with respect to each of the three PS elements 31 located at one (i.e., left-hand end in FIG. 5) of opposite ends of the array of PS elements 31 of the PW sensor 20. Similarly, the second-end area SR is approximated by summing the values obtained by subtracting the respective values on the reference curve $MTC_s$ from the corresponding values on the current curve MTC, with respect to each of the three PS elements 31 located at the other end (i.e., right-hand end in FIG. 5) of the array of PS elements 31. The optimum-portion area SM is approximated by summing the values obtained by subtracting the respective values on the reference curve $MTC_s$ from the corresponding values on the current curve MTC, with respect to each of the three PS elements 31 consisting of the optimum PS element 31a and two adjacent PS elements 31 located on both sides of the element 31a in the array of PS elements 31.

Step S14 is followed by Step S15 to calculate an overall amount of change, S, of the current curve MTC from the reference curve $MTC_s$, according to the following expression (1):

$$S = \sum_{i=0}^{29} |\{MTC(i) - \text{diff}\} - MTC_s(i)|,$$

where i: the serial number (No.) assigned to each PS element 31;

MTC(i): the value on the curve MTC with respect to the element 31 numbered "i";

$MTC_s(i)$: the value on the curve $MTC_s$ with respect to the element 31 numbered "i"; and diff: the value obtained by subtracting the value on the curve $MTC_s$ from the corresponding value on the curve MTC with respect to the optimum PS element 31a.

Figure 6:
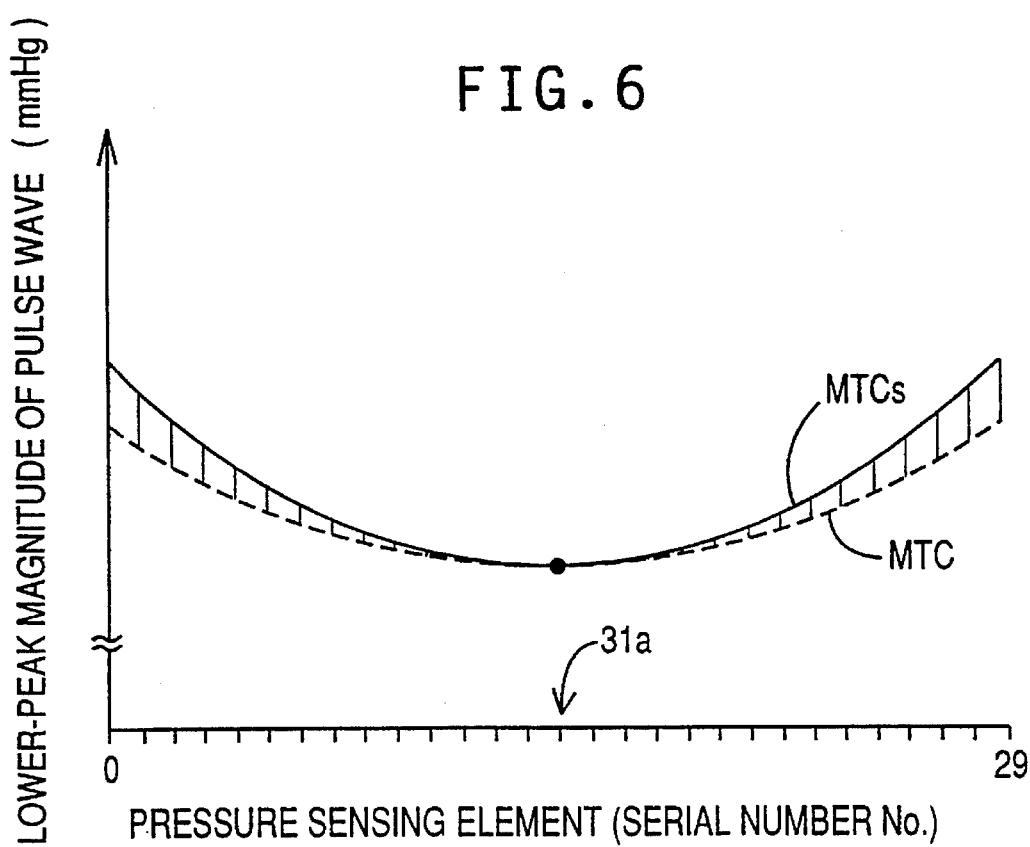
FIG. 6 is a view of (a) a reference curve $MTC_s$ and (b) a subsequent curve MTC translated so that the two curves $MTC_s$, MTC take an identical value with respect to an optimum pressure sensing element of the pulse wave sensor of FIG. 2.
Figure 7A:
FIGS. 7(a) to 7(j) are views of various patterns of change of a subsequent curve MTC from a reference curve $MTC_s$, each pattern belonging to a first group of patterns, I, which indicate that the pressing condition of the pulse wave sensor is stable.
Figure 7B:
Figure 7C:
Figure 7D:
Figure 7E:
Figure 7F:
Figure 7G:
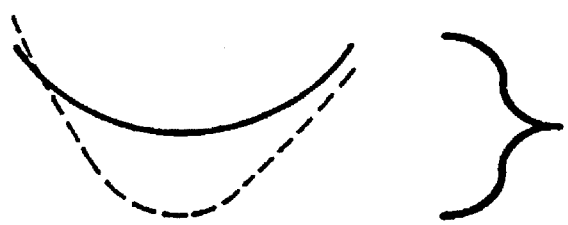
Figure 7H:
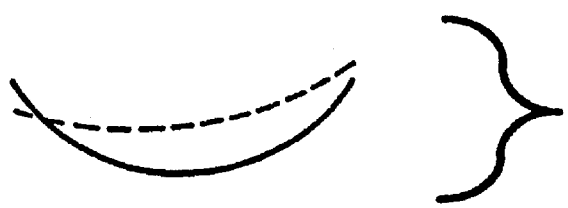
Figure 7I:
Figure 7J:
Figure 8A:
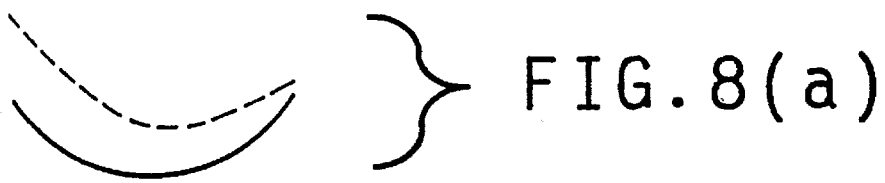
Figure 8B:
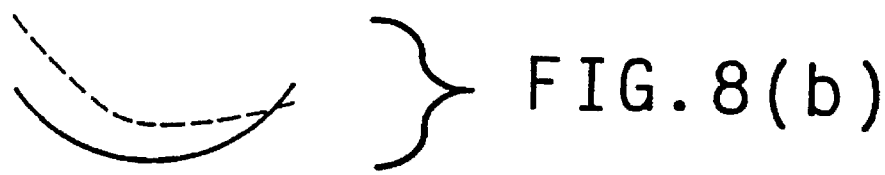
Figure 8C:
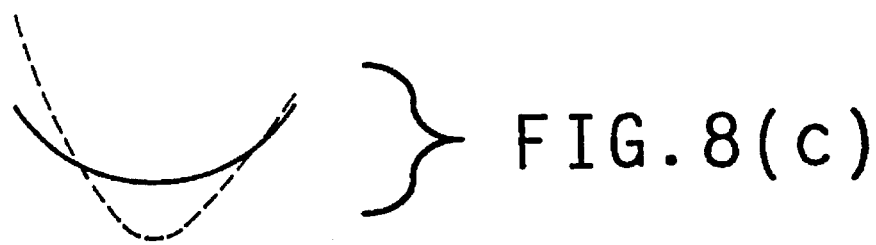
Figure 8D:
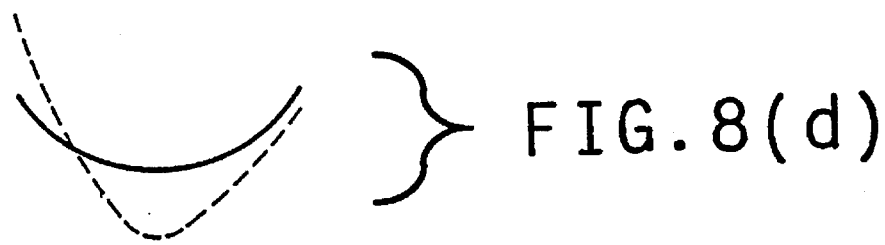
Figure 8E:
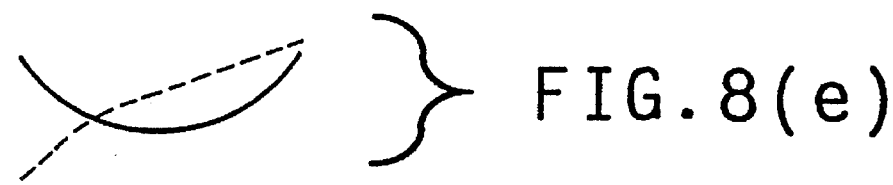
Figure 8F:
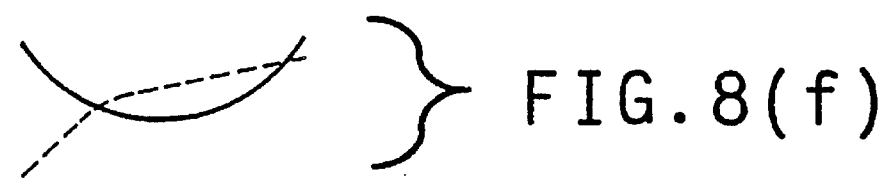
Figure 8G:
Figure 8H:
Figure 8I:
Figure 8J:
Figure 8K:
Figure 9A:
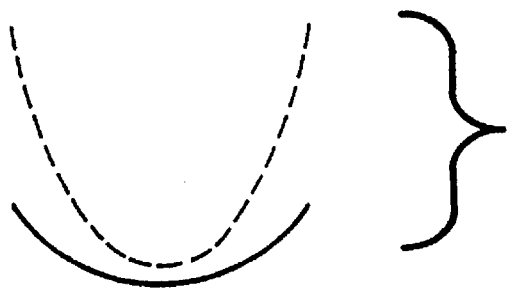
FIGS. 9(a) to 9(d) are views of various patterns of change of a subsequent curve MTC from a reference curve $MTC_s$, each pattern belonging to a third group of patterns, II, which indicate that the pressing condition of the pulse wave sensor is not stable.
Figure 9B:
Figure 9C:
Figure 9D:
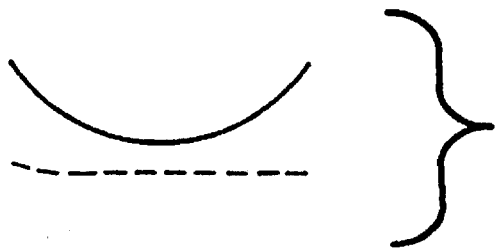

The change amount S approximates the change area enveloped by (a) the reference curve $MTC_s$ and (b) the current curve MTC translated along the axis of ordinate 52 by subtracting the value, diff, from the respective values on the curve MTC with respect to all the PS elements 31a, as shown in FIG. 6. In the coordinate system of FIG. 6, the two curves $MTC_s$, MTC take an identical value with respect to the optimum PS element.

At the following step, S16, in FIG. 4 (*a*), the CPU 34 judges whether the change area S is not greater than a first reference value, e.g., 80. A positive judgment at Step S16 that the change area S is not greater than 80 indicates that the change of the pulse waves (or pulse wave signals SM) represented by the change area S resulted from natural change of blood pressure of the subject 16 and therefore that the pressing condition of the PW sensor 20 against the body surface 12 is stable. Thus, the control of the CPU 34 goes to Step S17 to reset first and second counters $C_1$, $C_2$ each to zero ($C_1$=0, $C_2$=0). Then, the control of the CPU 34 returns to Step S3 to continue to detect the pressure pulse wave through the optimum PS element 31a. On the other hand, if a negative judgment is made at Step S16, the control of the CPU 34 goes to Step S18 to judge whether the change area S is greater than a second reference value, e.g., 400, greater than the first reference value employed at Step S16. A positive judgement at Step S18 that the change area S is greater than 400 indicates that the change of the pressure pulse wave represented by the change area S did not result from artificial change of blood pressure of the subject and therefore that the pressing condition of the PW sensor 20 against the body surface 12 is not stable. Thus, the control of the CPU 34 goes to Step S19 to reset first and second counters $C_1$, $C_2$ to $C_1$=0 and $C_2$=0, respectively. Then, the control of the CPU 34 returns to Step S1 to re-determine or update the optimum chamber pressure Pa, re-select or update the optimum PS element 31a, hold the chamber pressure P at the updated optimum pressure Pa, and resume detecting the pressure pulse wave of the subject through the updated optimum PS element 31a.

On the other hand, if a negative judgment is made at Step S18, i.e., if the change area S falls within the range, 80<S≦400, the control of the CPU 34 goes to Step S20 to judge whether the first-end area SL is equal to the optimum-portion area SM and simultaneously the optimum-portion area SM is equal to the second-end area SR. If a positive judgment is made at Step S20, the control goes to Step S21 to conclude that the pattern of change of the current curve MTC from the reference curve $MTC_s$ corresponds to a first group of patterns, I, more specifically, one of patterns shown in FIGS. 7(*a*) and 7(*b*). This result indicates that the pressing condition of the PW sensor 20 on the body surface 12 is stable. Therefore, the control of the CPU 34 goes to Step S17 to reset counters $C_1$, $C_2$ to $C_1$=0 and $C_2$=0, respectively, and subsequently returns to Step S3 to continue to detect the pressure pulse wave of the subject 16.

On the other hand, if a negative judgment is made at Step S20, the control of the CPU 34 goes to Step S22 to judge whether the absolute value of the first-end area SL is smaller than the absolute value of the optimum-portion area SM and simultaneously the absolute value of the optimum-portion area SM is greater than the absolute value of the second-end area SR. If a positive judgment is made at Step S22, the control goes to Step S21 to conclude that the pattern of change of the current curve MTC from the reference curve $MTC_s$ corresponds to the first pattern I, more specifically, one of patterns shown in FIGS. 7(*c*) to 7(*j*) wherein both of the end portions of the current curve MTC did not change from the corresponding portions of the reference curve $MTC_s$. This result indicates that the change of the pressure pulse wave represented by the change area S resulted from the change of blood pressure of the subject and that the pressing condition of the PW sensor 20 on the body surface 12 is stable. Therefore, the control of the CPU 34 goes to Step S17 to reset counters $C_1$, $C_2$ to $C_1$=0 and $C_2$=0, respectively, and subsequently returns to Step S3 to continue to detect the pressure pulse wave of the subject 16.

On the other hand, if a negative judgment is made at Step S22, the control of the CPU 34 goes to Step S23 to judge whether the absolute value of the first-end area SL is greater than the absolute value of the optimum-portion area SM and simultaneously the absolute value of the optimum-portion area SM is smaller than the absolute value of the second-end area SR. If a positive judgment is made at Step S23, the control goes to Step S24 to judge whether the product of the first-end area SL and the second-end area SR is negative, i.e., judge whether one of the two areas SL, SR is negative and the other area SL, SR is positive.

If a positive judgment is made at Step S24, the control goes to Step S25 to conclude that the pattern of change of the current curve MTC from the reference curve $MTC_s$ corresponds to a second group of patterns, II, more specifically, one of patterns shown in FIGS. 8(*i*) to 8(*l*) wherein both of the end portions of the current curve MTC largely changed from the corresponding portions of the reference curve $MTC_s$. This result suggests that the change of the pressure pulse wave represented by the change area S did not result from the change of blood pressure of the subject and that the pressing condition of the PW sensor 20 is not stable, i.e., has changed. Subsequently, the control of the CPU 34 goes to Step S26 to judge whether the change area S is greater than a third reference value, e.g., 150, greater than the first reference value used at Step S16 and smaller than the second reference value used at Step S18. A positive judgement at Step S26 that the change area S is greater than 150, indicates that the pressing condition of the PW sensor 20 against the body surface 12 has not changed, i.e., remains stable. Thus, the control of the CPU 34 goes to Step S27 to reset counter $C_2$ to $C_2=0$, and respectively. Then, the control of the CPU 34 returns to Step S3 to continue to detect the pressure pulse wave of the subject 16.

On the other hand, if a positive judgment is made at Step S26, the control of the CPU 34 goes to Step S28 to add one to the content of second counter $C_2$. The content of counter $C_2$ indicates the number of positive judgment or judgements made at Step S26. Subsequently the control goes to Step S29 to judge whether the content of counter $C_2$ is two (i.e., $C_2=2$). If a negative judgment is made at Step S29, i.e., if the content of counter $C_2$ is $C_2=1$, it cannot readily be concluded that the pressing condition of the PW sensor 20 against the body surface 12 has changed, i.e., the pressing condition may remain stable. Thus, the control returns to Step S3. On the other hand, if a positive judgment is made at S29, it can be concluded that the pressing condition of the PW sensor 20 has changed. Thus, the control goes to Step S30 to reset the content of counter $C_2$ to $C_2=0$, and subsequently returns to Step S1 to update the optimum chamber pressure Pa and the optimum PS element 31a, hold the chamber pressure P at the updated optimum pressure Pa, and resume detecting the pressure pulse wave of the subject 16 through the updated optimum PS element 31a.

Meanwhile, if a negative judgment is made at Step S23, the control of the CPU 34 goes to Step S25 to conclude that the pattern of change of the curve MTC from the curve $MTC_s$ corresponds to the second pattern, II, more specifically, one, of patterns shown in FIGS. 8(a) to 8(h) wherein one of the end portions of the current curve MTC largely changed from the corresponding portion of the reference curve $MTC_s$. This result suggests that the change of the pressure pulse wave represented by the change area S did not result from the change of blood pressure of the subject and that the pressing condition of the PW sensor 20 has changed.

If a negative judgment is made at Step S24, i.e., if the first-end area SL and the second-end area SR are both positive or both negative, the control of the CPU 34 goes to Step S31 to conclude that the pattern of change of the current curve MTC from the reference curve $MTC_s$ corresponds to a third pattern, III, i.e., one of patterns shown in FIGS. 9(a) to 9(d) wherein both of the end portions of the current curve MTC largely changed from the corresponding portions of the reference curve $MTC_s$. This result suggests that the change of the pressure pulse wave represented by the change area S did not result from the change of blood pressure of the subject and that the pressing condition of the PW sensor 20 has changed. Step S31 is followed by Step S32 to judge whether the change area S is greater than, e.g., 80. A negative judgment at Step S32 indicates that the pressing condition of the PW sensor 20 has not changed, i.e., remains stable. Therefore, the control of the CPU 34 goes to Step S33 to reset the content of first counter $C_1$ to $C_1=0$, and subsequently returns to Step S3 to continue to detect the pressure pulse wave of the subject 16.

On the other hand, if a positive judgment is made at Step S32, the control of the CPU 34 goes to Step S34 to add one to the content of first counter $C_1$, and subsequently to Step S35 to judge whether the content of counter $C_1$ is two (i.e., $C_1=2$). The counter $C_1$ counts the number of positive judgment or judgments made at Step S32. If a negative judgment is made at Step S35, i.e., if the content of counter $C_1$ is $C_1=1$, it cannot readily be concluded that the pressing condition of the PW sensor 20 against the body surface 12 has changed, i.e., it may remain stable. Thus, the control returns to Step S3. On the other hand, if a positive judgment is made at S35, it can be concluded that the pressing condition of the PW sensor 20 against the body surface 12 has changed. Thus, the control goes to Step S36 to reset the content of first counter $C_1$ to $C_1=0$ and subsequently returns to Step S1 and following steps to update the optimum chamber pressure Pa and the optimum PS element 31a, hold the chamber pressure P at the updated optimum pressure Pa, and resume detecting the pressure pulse wave of the subject 16 through the updated optimum PS element 31a. In the present embodiment, Steps S14–S36 and a portion of the control device 32 to carry out those steps cooperate with each other to serve as judging means for judging whether the pressing condition of the PW sensor 20 on the body surface 12 is stable, based on the change amount S of the current curve MTC from the reference curve $MTC_s$.

As is apparent from the foregoing description, after the beginning of the pulse wave detection with the PW sensor 20 (i.e., optimum PS element 31a) pressed at the optimum pressing force Pa, the present apparatus periodically judges whether the pressing condition of the PW sensor 20 against the body surface 12 remains stable, based on the amount of change S and/or pattern of change SL, SM, SR of each subsequent curve MTC from the reference curve $MTC_s$ obtained under the stable pressing condition of the PW sensor 20 immediately after the PW sensor 20 is held at the optimum pressure Pa. If a negative judgment is made, the apparatus re-starts the pulse wave detection after re-determining the optimum pressing force Pa. Thus, the pressing condition of the PW sensor 20 with respect to the body surface 12 is adjusted, and therefore the apparatus continuously detects the pressure pulse wave with high accuracy.

While the present invention has been described in its preferred embodiment, the invention may otherwise be embodied.

While in the illustrated embodiment both (a) the change area S representing the change amount of the current curve MTC from the reference curve $MTC_s$ and (b) the three partial areas SL, SM, SR used to identify the change pattern of the curve MTC from the curve $MTC_s$ are utilized for judging whether the pressing condition of the PW sensor 20 against the body surface 12 is stable, it is possible to utilize only one of the two parameters (a) and (b) for the same purpose.

Although in the illustrated embodiment the current curve MTC is translated so that the respective values of the current and reference curves MTC, $MTC_s$ with respect to the optimum PS element 31a coincide with each other, it is possible to translate the curve MTC so that the respective values of the two curves MTC, $MTC_s$ with respect to a predetermined reference PS element 31 (e.g., a middle one in the array) coincide with each other in the coordinate system of FIG. 5.

While in the illustrated embodiment a curve MTC determined immediately after the chamber pressure P is held at the optimum pressure Pa is used as the reference curve $MTC_s$, it is possible to use as the reference curve $MTC_s$ a preceding curve MTC determined in a control cycle preceding a current control cycle where a current curve MTC is determined. In this case, too, the apparatus judges whether the pressing condition of the PW sensor 20 is stable, based on change of the current curve MTC from the reference curve $MTC_s$, i.e., preceding curve MTC.

Figure 3A:
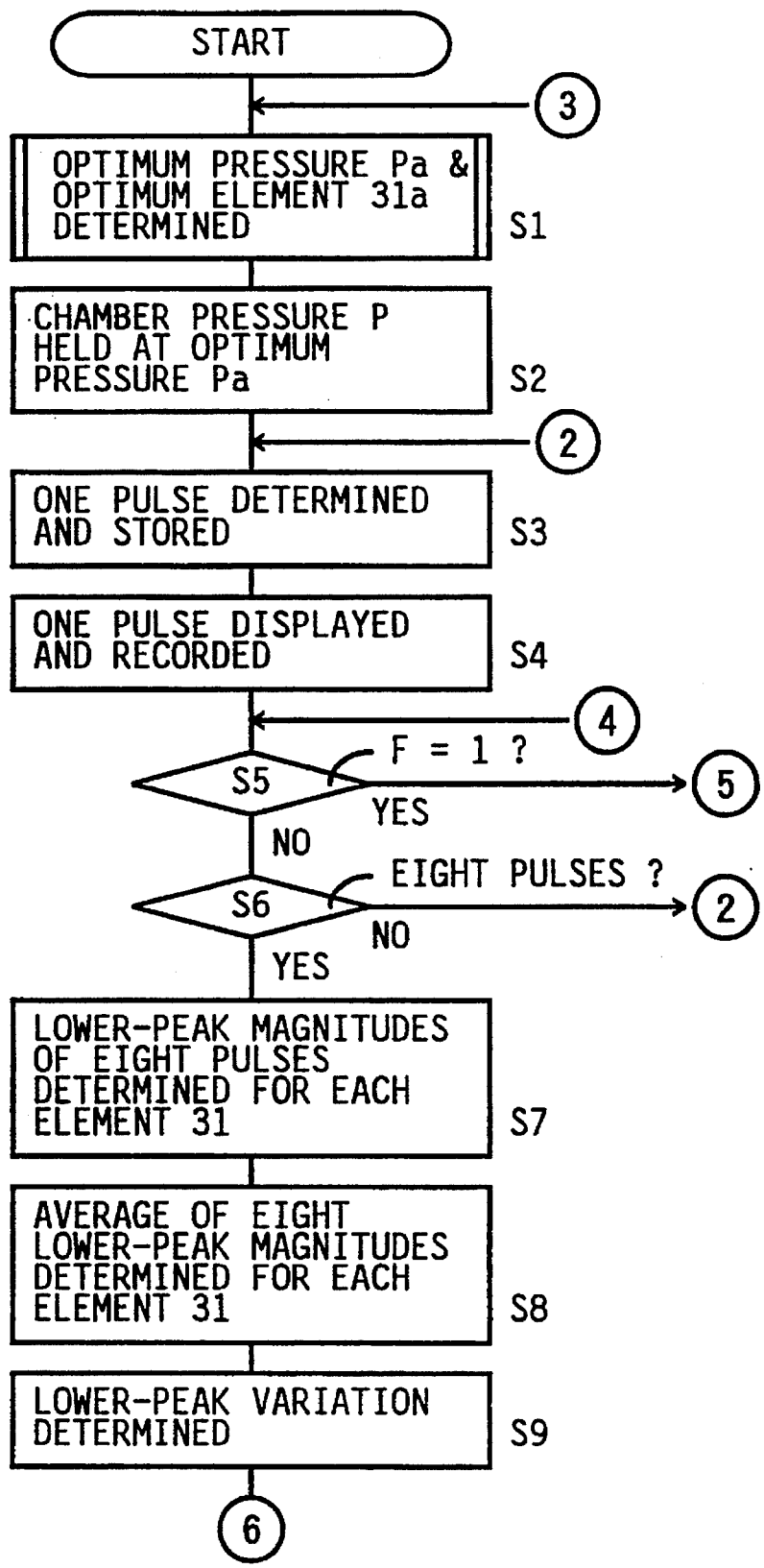
FIGS. 3(a) and 3(b) are flow charts representing respective parts of the control program used by the apparatus of FIG. 1.
Figure 3B:
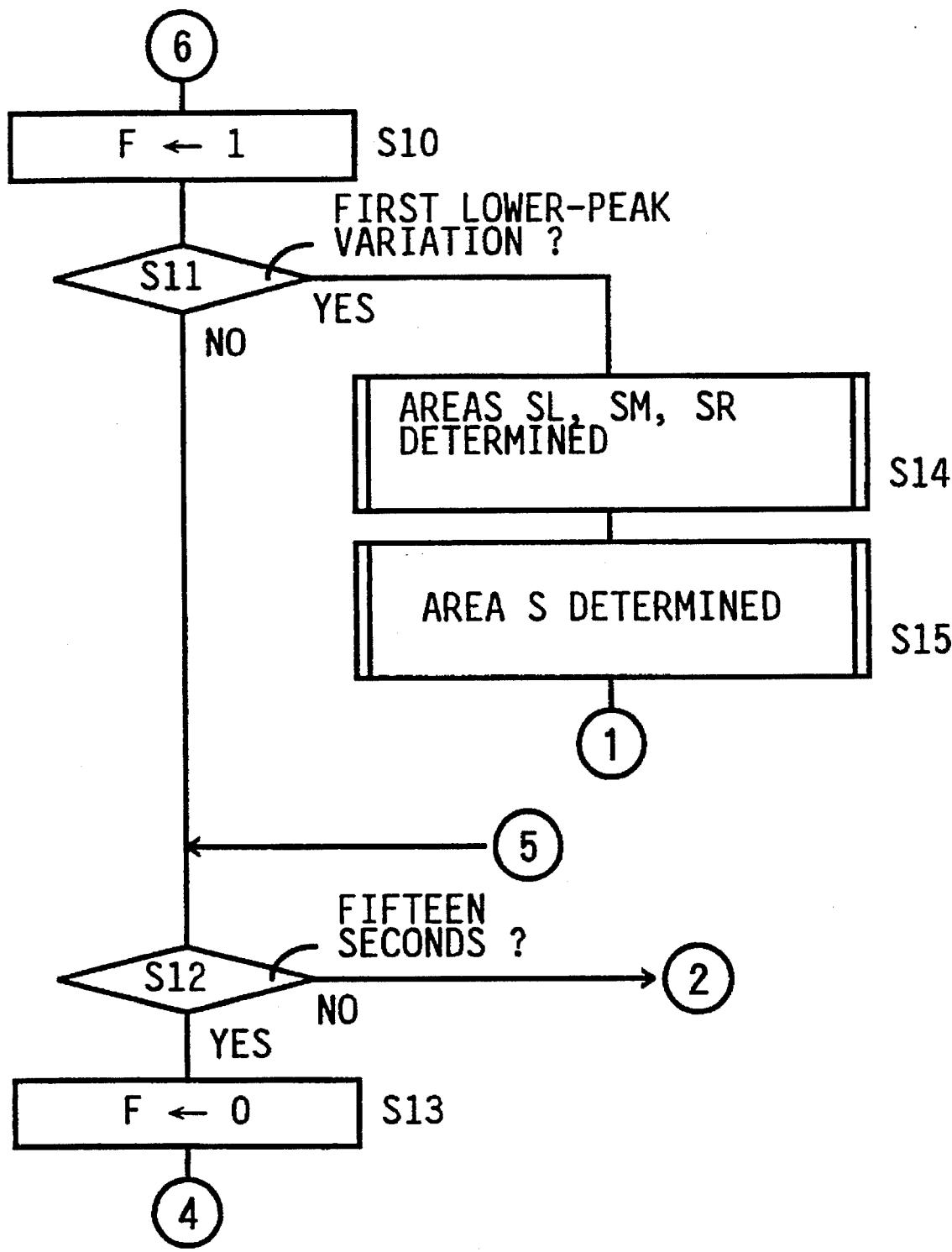

Although in the illustrated embodiment the apparatus re-starts with Step S1 of FIG. 3(a) when it judges that the pressing condition of the PW sensor 20 is not stable, it is alternatively possible to command the display/record device 40 to display an indication that the pressing condition of the PW sensor 20 has changed, and thereafter terminate the current pulse wave detecting operation. The apparatus may be provided with an alarm device which issues an alarm sound in the same event.

Figure 4A:
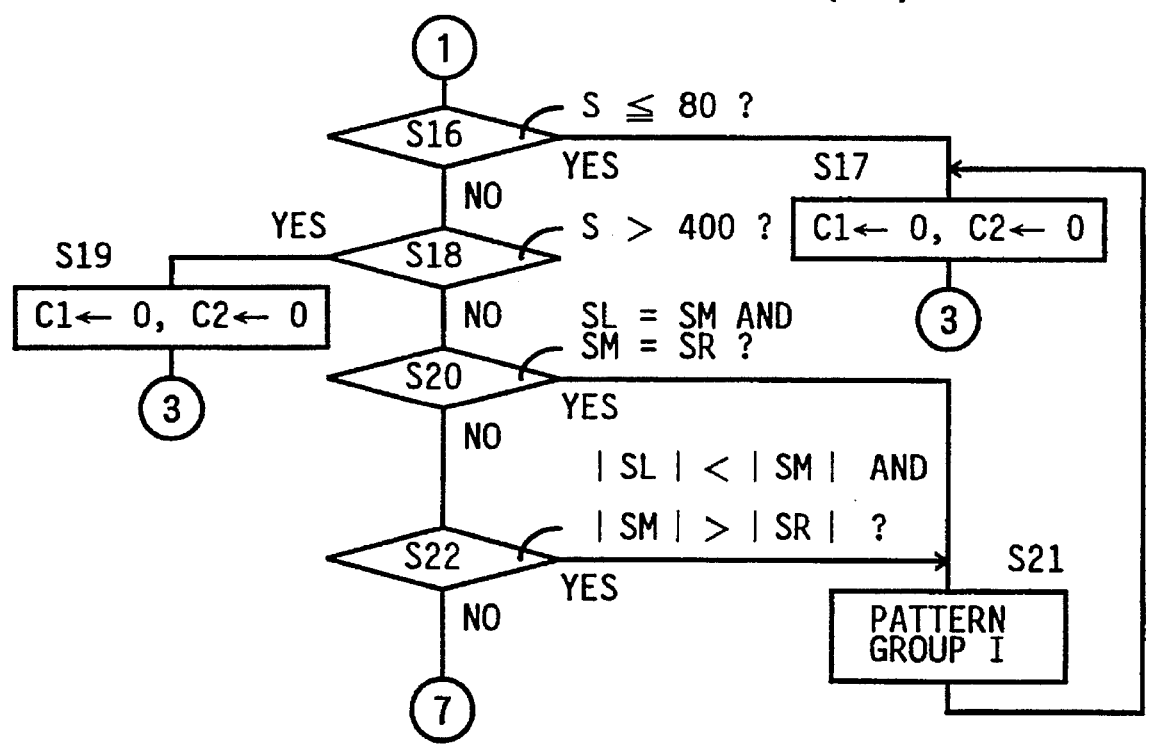
FIGS. 4(a) and 4(b) are flow charts representing other parts of the control program used by the apparatus of FIG. 1.
Figure 4B:
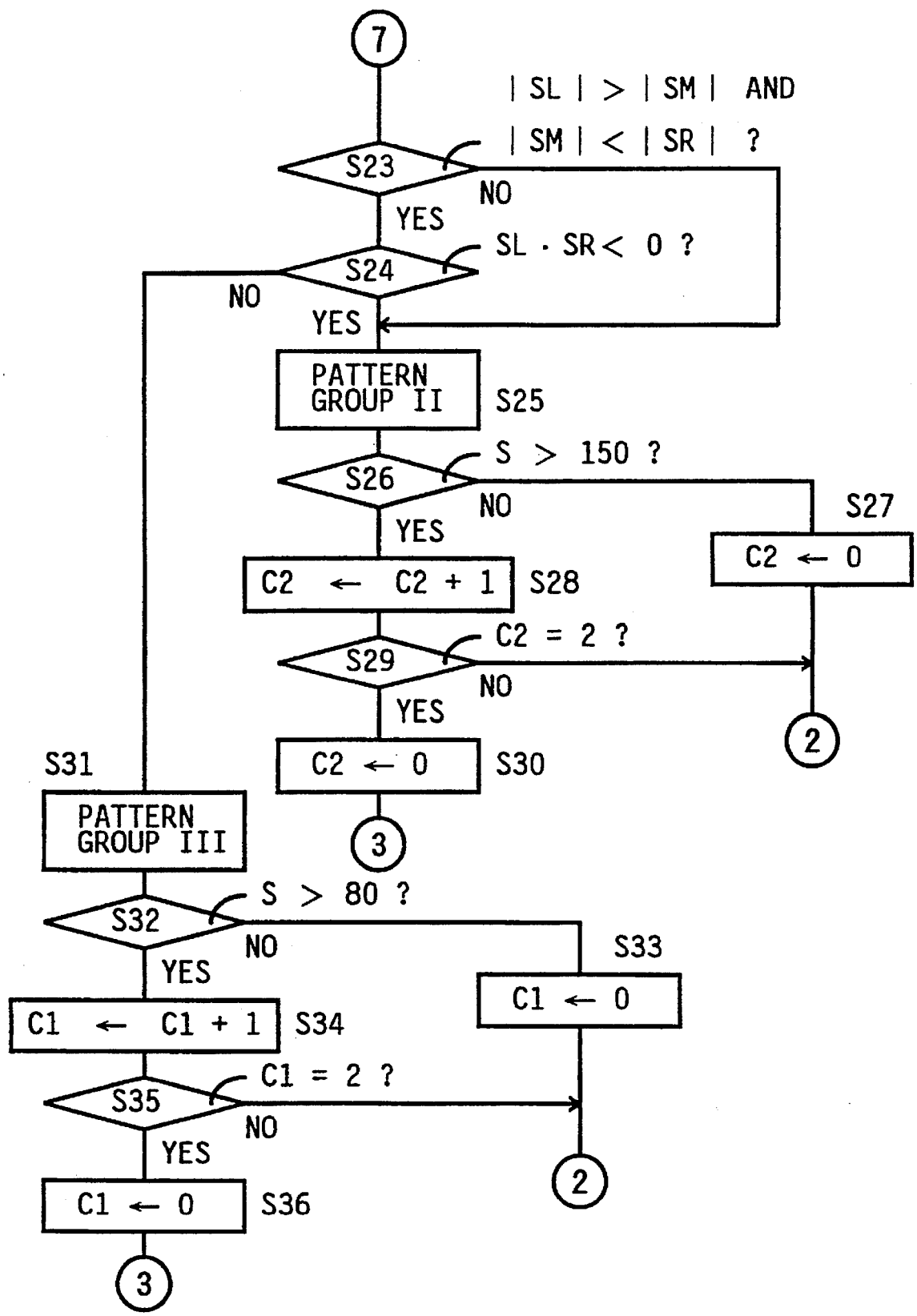

In the illustrated embodiment, Steps S21, S25, and S31 may be omitted from the flow chart of FIGS. 4(a) and 4(b).

While in the illustrated embodiment a curve MTC is iteratively determined at regular intervals of 15 seconds based on an average value of respective lower-peak magnitudes of eight pulses of the pulse wave signal SM from each of the PS elements 31, it is alternatively possible to iteratively determine a curve MTC based on a lower-peak magnitude of a single pulse of the signal SM from each PS element 31, either at regular intervals of time or for every pulse of the signal SM (i.e., pressure pulse wave of the subject 16).

The illustrated pulse wave detecting apparatus may further incorporate a displacing device as disclosed in U.S. Pat. No. 4,901,733. The displacing device includes a motor and a feed screw, and is advantageously used for positioning the PW sensor 20 in a direction intersecting the direction of extension of the radial artery 30. When the apparatus judges that the pressing condition of the PW sensor 20 is not stable, the apparatus may re-position, by operating the displacing device, the PW sensor 20 relative to the radial artery 30 before re-starting with Step S1 of FIG. 3(a).

While in the illustrated embodiment the display/record device 40 displays and records the pressure pulse wave detected through the optimum PS element 31a, the apparatus may further incorporate a blood pressure measuring device including an inflatable cuff for measuring an actual blood pressure value or values of the subject. In this case, the apparatus may be provided with means for determining, in place of or in addition to the pulse-wave display and record functions, a relationship between blood pressure (BP) and pulse-wave magnitude (PW) based on (a) the measured BP value or values and (b) the PW magnitude or magnitudes detected through the PW sensor 20 (i.e., optimum PS element 31a) and continuously determine the BP value or values of the subject 16 for each pulse of the pulse wave of the subject 16 according to the determined BP-PW relationship. This process is described in detail in, for example, U.S. Pat. No. 5,099,853.

It is to be understood that the present invention may be embodied with other changes, modifications, and improvements that may occur to those skilled in the art without departing from the scope and spirit of the invention defined in the appended claims.

What is claimed is:

1. A pulse wave detecting apparatus for detecting a pulse wave from a living subject, the pulse wave comprising a plurality of pulses, each pulse produced from an arterial vessel of the subject in synchronism with a heartbeat of the subject, comprising:

a pulse wave sensor having a press surface and including at least one array of pressure sensing elements provided in said press surface, said press surface of said pulse wave sensor being adapted to be pressed against said arterial vessel of said living subject via a body surface of said subject such that a direction of said array of pressure sensing elements intersects a direction of extension of said arterial vessel, so that each of said pressure sensing elements detects said pulse wave produced from said arterial vessel and generates a pulse wave signal representing the detected pulse wave;

a pressing device which produces a pressing force to press said press surface of said pulse wave sensor against said arterial vessel via said body surface;

regulating means for changing said pressing force of said pressing device applied to said pulse wave sensor, determining an optimum value of said pressing force based on at least one of the pulse wave signals generated from said pressure sensing elements, and holding said pressing force of said pressing device at the thus determined optimum value;

lower-peak variation determining means for determining a lower peak of at least one pulse of each of the respective pulse wave signals from said pressure sensing elements, said lower-peak variation determining means iteratively determining a variation of the respective lower peaks of said pulse wave signals with respect to said array of pressure sensing elements after said pressing force of said pressing device is held at said optimum value; and judging means for judging whether a pressing condition of said pulse wave sensor on said body surface is stable, based on change of the lower-peak variations determined by said lower-peak variation determining means.

2. An apparatus according to claim 1, further comprising control means for controlling, when said judging means provides a negative judgment that said pressing condition of said pulse wave sensor is not stable, said regulating means to update said optimum value of said pressing force and hold said pressing force at the thus updated optimum value.

3. An apparatus according to claim 1, wherein said regulating means determines, while changing said pressing force of said pressing device, an amplitude of said at least one pulse of the respective pulse wave signals from said pressure sensing elements, selects a maximum pulse having a maximum amplitude from said pulses of said at least one pulse wave signal, and determines as said optimum value of said pressing force a pressing force of said pressing device at a time of detection of said maximum pulse.

4. An apparatus according to claim 1, wherein said regulating means determines, while changing said pressing force of said pressing device, an amplitude of each of the respective pulse wave signals from said pressure sensing elements, selects a maximum pulse having a maximum amplitude from said pulses of said each pulse wave signal, and determines as an optimum pressure sensing element one of said pressure sensing elements which has detected said maximum pulse.

5. An apparatus according to claim 4, further comprising an output means comprising at least one of (a) display means for displaying a waveform of the pulse wave represented by the pulse wave signal supplied from said optimum pressure sensing element and (b) recorder means for recording a waveform of the pulse wave represented by the pulse wave signal supplied from said optimum pressure sensing element.

6. An apparatus according to claim 1, wherein said regulating means holds said pressing force of said pressing device, at said optimum value, so that said press surface of said pulse wave sensor partially flattens a wall of said arterial vessel and said pressure sensing elements detect said pulse wave through the flattened wall of said arterial vessel.

7. An apparatus according to claim 1, wherein said lower-peak variation determining means determines a lower peak of each of a predetermined number of pulses of each of said pulse wave signals from said pressure sensing elements in each of a plurality of determination cycles, said lower-peak variation determining means determining an average of said predetermined number of lower peaks of said each pulse wave signal and determining a variation of the respective averages of said pulse wave signals with respect to said array of pressure sensing elements, in said each cycle.

8. An apparatus according to claim 1, wherein said lower-peak variation determining means comprises:

means for determining, as a reference variation, a variation of respective lower peaks of said pulse wave signals with respect to said array of pressure sensing elements in one of a plurality of determination cycles; and means for determining, as a current variation, a variation of respective lower peaks of said pulse wave signals with respect to said array of pressure sensing elements in a current one of said cycles subsequent to said one cycle.

9. An apparatus according to claim 8, wherein said judging means comprises:

first means for determining a difference between a lower peak of at least one pulse of the pulse wave signals from each of a first group of pressure sensing elements determined in said one cycle and a lower peak of at least one pulse of the pulse wave signals from said each pressure sensing element of said first group determined in said current cycle, and obtaining a first amount of change by summing the respective differences determined for said pressure sensing elements of said first group;

second means for determining a difference between a lower peak of at least one pulse of the pulse wave signals from each of a second group of pressure sensing elements determined in said one cycle and a lower peak of at least one pulse of the pulse wave signals from said each pressure sensing element of said second group determined in said current cycle, and obtaining a second amount of change by summing the respective differences determined for said pressure sensing elements of said second group;

third means for determining a difference between a lower peak of at least one pulse of the pulse wave signals from each of a third group of pressure sensing elements determined in said one cycle and a lower peak of at least one pulse of the pulse wave signals from said each pressure sensing element of said third group obtained in said current cycle, and obtaining a third amount of change by summing the respective differences determined for said pressure sensing elements of said third group;

said array of pressure sensing elements including said first, second, and third groups of pressure sensing elements such that said first, second, and third groups do not overlap each other in said array;

fourth means for comparing said first, second, and third amounts of change with each other; and fifth means for judging whether said pressing condition of said pulse wave sensor is stable, based on the comparison results obtained by said fourth means.

10. An apparatus according to claim 8, wherein said judging means comprises:

first means for determining a difference between a lower peak of at least one pulse of the pulse wave signals determined in said one cycle and a lower peak of at least one pulse of the pulse wave signals determined in said current cycle, obtaining a new lower peak by subtracting said difference from each of the respective lower peaks of said pulse wave signals from said pressure sensing elements determined in said current cycle, and obtaining an overall amount of change of said current variation from said reference variation by summing respective values obtained by subtracting the respective new lower peaks from corresponding lower peaks of said pulse wave signals from said pressure sensing elements determined in said one cycle;

second means for comparing said overall amount of change with a first reference value; and third means for judging that said pressing condition of said pulse wave sensor is stable, when said overall amount of change is smaller than said first reference value.

11. An apparatus according to claim 10, wherein said judging means further comprises:

fourth means for comparing said overall amount of change with a second reference value greater than said first reference value; and fifth means for judging that said pressing condition of said pulse wave sensor is not stable, when said overall amount of change is greater than said second reference value.

* * * * *